(12) United States Patent
De Cicco et al.

(10) Patent No.: US 7,648,475 B2
(45) Date of Patent: Jan. 19, 2010

(54) NON-INVASIVE DEVICE FOR MEASURING BLOOD TEMPERATURE IN A CIRCUIT FOR THE EXTRACORPOREAL CIRCULATION OF BLOOD, AND EQUIPMENT PROVIDED WITH THIS DEVICE

(75) Inventors: Giorgio De Cicco, Modena (IT); Francesco Fontanazzi, Modena (IT); Annalisa Delnevo, Sant'Agata Bolognese (IT); Massimo Zaccarelli, San Felice sul Panaro (IT); Francesco Paolini, Ganaceto (IT)

(73) Assignee: Gambro Lundia AB (SE)

( * ) Notice: Subject to any disclaimer, the term of this patent is extended or adjusted under 35 U.S.C. 154(b) by 787 days.

(21) Appl. No.: 10/500,336

(22) PCT Filed: Dec. 20, 2002

(86) PCT No.: PCT/IB02/05572

§ 371 (c)(1),
(2), (4) Date: Jun. 28, 2004

(87) PCT Pub. No.: WO03/055544

PCT Pub. Date: Jul. 10, 2003

(65) Prior Publication Data

US 2005/0094704 A1    May 5, 2005

(30) Foreign Application Priority Data

Dec. 28, 2001    (IT) .......................... MI2001A2828

(51) Int. Cl.
*A61M 37/00* (2006.01)
*A61M 31/00* (2006.01)
*A61M 1/00* (2006.01)
*C02F 1/00* (2006.01)

(52) U.S. Cl. ..................... 604/4.01; 604/5.01; 604/6.09; 604/65; 604/67; 422/44; 210/742; 210/741

(58) Field of Classification Search ................ 604/4.01, 604/5.01, 6.11, 6.14, 609, 65, 67, 6.13, 28; 422/1, 4, 44, 45, 46, 48; 210/742, 741, 143, 210/86, 87; 417/2–6, 18–22, 42, 43, 44.1
See application file for complete search history.

(56) References Cited

U.S. PATENT DOCUMENTS 4,091,672 A    5/1978    Amrine et al.

(Continued)

FOREIGN PATENT DOCUMENTS

EP    0 231 652 A2    8/1987

(Continued)

*Primary Examiner*—Jacqueline F. Stephens
(74) *Attorney, Agent, or Firm*—Finnegan, Henderson, Farabow, Garrett & Dunner L.L.P.

(57) ABSTRACT

A non-invasive device for measuring blood temperature in a circuit for the extracorporeal circulation of blood includes a line in which blood taken from a patient flows. The device also includes a temperature sensor connected to the line and provided with a device for measuring the intensity of an electromagnetic radiation. The measuring device faces a connecting portion or window of the line that is permeable by electromagnetic radiation in a first wave band, and generates a first signal, correlated with the electromagnetic radiation in the first band and therefore with the temperature of the blood flowing in the line.

28 Claims, 3 Drawing Sheets

U.S. PATENT DOCUMENTS

| | | | |
|---|---|---|---|
| 4,243,883 A | 1/1981 | Schwarzmann |
| 4,444,498 A | 4/1984 | Heinemann |
| 4,774,415 A | 9/1988 | Biegel et al. |
| 4,894,164 A | 1/1990 | Polaschegg |
| 5,150,969 A | 9/1992 | Goldberg et al. |
| 5,154,512 A | 10/1992 | Schietinger et al. |
| 5,180,896 A | 1/1993 | Gibby et al. |
| 5,211,626 A | 5/1993 | Frank et al. |
| 5,261,874 A | 11/1993 | Castle |
| 5,539,673 A | 7/1996 | Charm et al. |
| 5,588,959 A | 12/1996 | Ahmad et al. |
| 5,615,672 A | 4/1997 | Braig et al. |
| 6,283,632 B1 | 9/2001 | Takaki |
| 6,439,577 B2 | 8/2002 | Jorgensen et al. |

FOREIGN PATENT DOCUMENTS

| | | |
|---|---|---|
| EP | 0 364 579 A1 | 4/1990 |
| EP | 0 720 013 A2 | 7/1996 |
| EP | 1 132 101 A1 | 9/2001 |
| JP | 3-273689 | 12/1991 |
| JP | 9-257584 | 10/1997 |
| JP | 2000-186963 | 7/2000 |
| JP | 2000-214083 | 8/2000 |
| JP | 2001-349783 | 12/2001 |
| WO | WO 92/13482 | 8/1992 |
| WO | WO 93/06775 | 4/1993 |
| WO | WO 93/23747 | 11/1993 |
| WO | WO 94/01749 | 1/1994 |
| WO | WO 94/12859 | 6/1994 |
| WO | WO 94/27495 | 12/1994 |
| WO | WO 95/04266 | 2/1995 |
| WO | WO 96/04535 | 2/1996 |
| WO | WO 98/38953 | 9/1998 |
| WO | WO 98/52629 | 11/1998 |
| WO | WO 01/33214 A2 | 5/2001 |
| WO | WO 01/33214 A3 | 5/2001 |

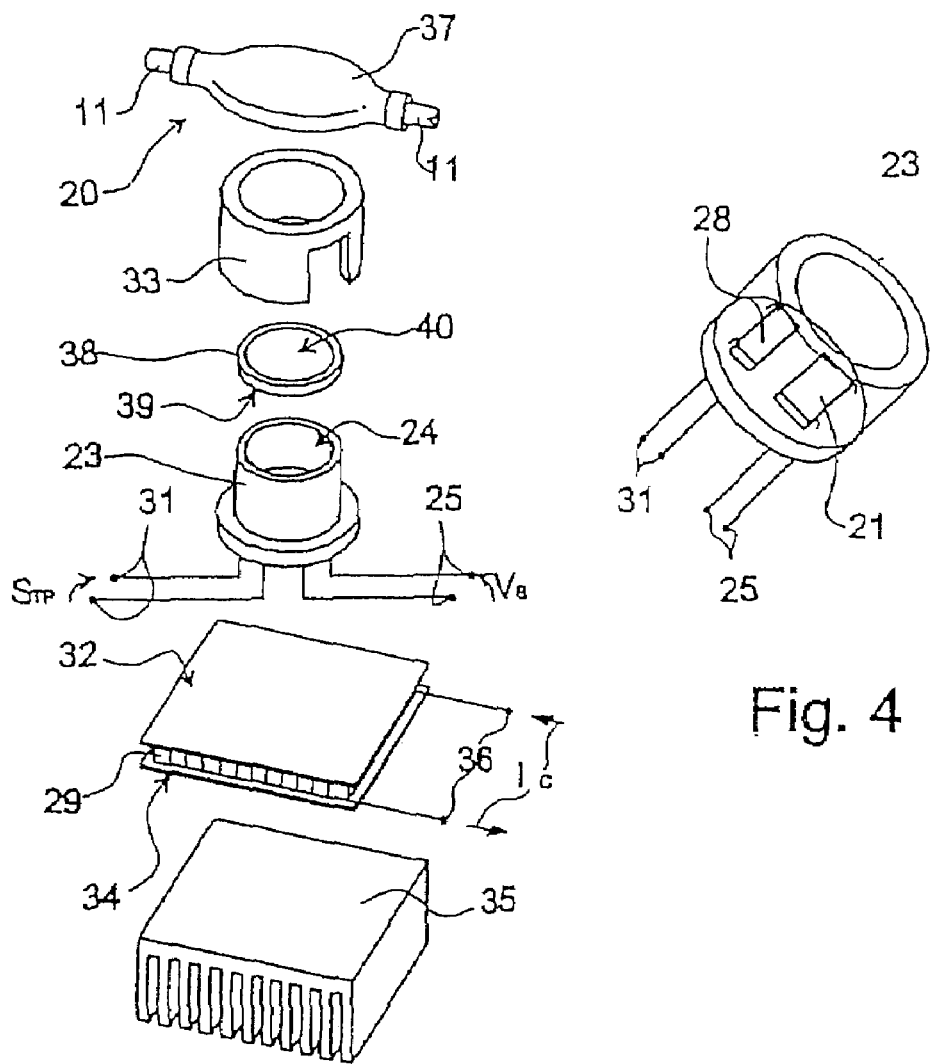
Fig. 3
Fig. 4
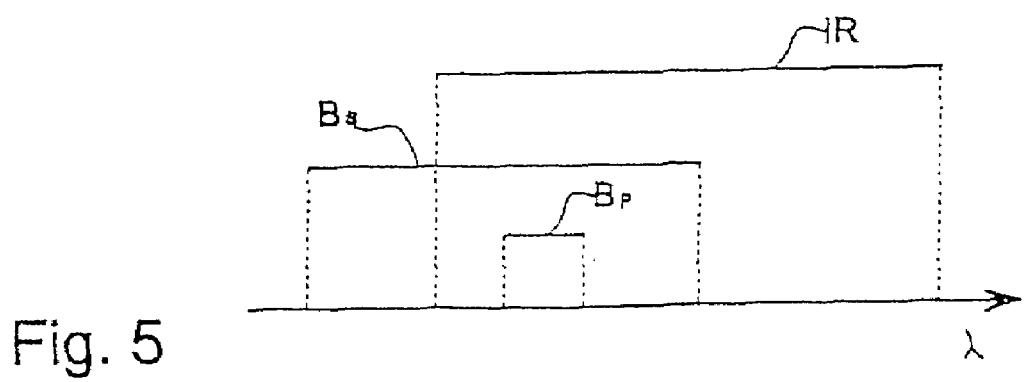
Fig. 5

NON-INVASIVE DEVICE FOR MEASURING BLOOD TEMPERATURE IN A CIRCUIT FOR THE EXTRACORPOREAL CIRCULATION OF BLOOD, AND EQUIPMENT PROVIDED WITH THIS DEVICE

The present invention relates to a non-invasive device for measuring blood temperature in a circuit for the extracorporeal circulation of blood, and to equipment provided with this device.

It is known that one of the problems closely associated with the use of circuits for the extracorporeal circulation of blood is that of monitoring the blood temperature. This is because the human body maintains the blood temperature at an essentially constant level of approximately 37° C., with very limited variations contained within a few tenths of a degree Celsius (in non-pathological conditions). Larger variations can result in an imbalance in the body, causing damage which may be severe. However, during its extracorporeal circulation, the blood gives up some of its heat to the surrounding environment, and this may result in excessive and prolonged lowering of the blood temperature, such that metabolic imbalance is caused, especially in vulnerable patients.

Special arrangements must therefore be made for certain types of machines, such as dialysis machines, which use a circuit for extracorporeal circulation. Dialysis treatments have to be repeated frequently and for prolonged periods, and it is therefore particularly important to protect the patient from the risks described above. Moreover, a dialysis machine uses a filter having a first compartment, in which the blood flows, and a second compartment, in which there flows a dialysate which may be at a temperature different from the blood temperature. The two compartments are separated from each other by a semi-permeable membrane which allows heat to be transferred from the blood to the dialysate and vice versa. For this reason also, the problem of monitoring the blood temperature is very important in the field of dialysis machines. Similar problems arise when haemofiltration and haemodiafiltration treatments are carried out.

Various methods have been proposed for monitoring the blood temperature during extracorporeal circulation, the efficacy of these methods being dependent oil the possibility of measuring in a precise and rapid way the patient's blood temperature immediately downstream of the collection point and upstream of the return point. This temperature is measured indirectly by means of a non-invasive measurement system comprising a temperature sensor connected to a portion of the extracorporeal circuit. In greater detail, in known measurement systems a portion of a line of the extracorporeal circuit is housed in an aluminium element shaped in such a way that it has a large heat exchange surface in contact with the said line. A platinum thermistor is placed in contact with the aluminium element and is used to measure the temperature of the latter. In conditions of thermal equilibrium, the temperature of the line and therefore of the blood flowing in it is related to the temperature of the aluminium element by a known relation and can be determined from the signal supplied by the thermistor. In order to reduce the effect of the external environment on the result of the measurement, the transducer formed in this way (the aluminium element and the thermistor) is inserted into a support, also made from aluminium, which is kept at the same temperature as the line by a heater controlled by a suitable control unit. Thus the heat exchange between the transducer and the external environment is minimized, and the measured temperature depends solely on the heat exchange with the line. The space between the transducer and the heated support is filled with a material (for example, PVC) chosen in such a way as to optimize the compromise between tire speed of response of the sensor and the thermal insulation from the external environment.

However, the known systems have a number of drawbacks. This is because the lines forming the extracorporeal circuit are normally made from material with low thermal conductivity, in order to prevent a damaging loss of heat. The thermal coupling between the blood flowing within the extracorporeal circuit and the aluminum element is therefore poor, and the measurement made in the way that has been described is inevitably of low accuracy. In particular, the known systems have very long response transients, since a variation in blood temperature is detected only after a new state of thermal equilibrium has been established among the blood flow, the wall of the extracorporeal circuit, the transducer and the heated support.

The object of the present invention is to provide a non-invasive device for measuring the blood temperature in a circuit for the extracorporeal circulation of blood, which is free of the drawbacks of the known art.

According to the present invention, a non-invasive device is provided for measuring blood temperature in a circuit for the extracorporeal circulation of blood, this device comprising a line in which blood taken from a patient flows, and a temperature sensor, connected to the said line and generating a first signal correlated with the temperature of the blood flowing in the said line, characterized in that the said temperature sensor comprises a device for measuring the intensity of an electromagnetic radiation, and the said line comprises a connecting portion facing the said measuring device and permeable by electromagnetic radiation in a first wave band; the said first signal being correlated with the intensity of the said electromagnetic radiation in the said first band.

The device according to the invention advantageously permits the measurement of a quantity directly correlated with the patient's blood temperature, namely the electromagnetic radiation emitted by the blood at a certain temperature in a predetermined frequency band. Secondly, the portion of the extracorporeal circuit on which the measurement is made is connected to the sensor in such a way that the fraction of electromagnetic radiation emitted by the blood and incident on the measuring device is maximized. Furthermore, the devices for measuring electromagnetic radiation, comprising a thermopile in a preferred embodiment of the invention, have very short response transients. The device therefore has very high precision, accuracy and speed of response. In practice, the blood temperature can be measured with an error of less than 0.1° C. and with transients of the order of hundredths of a second.

The present invention also relates to control equipment in an extracorporeal blood circuit, as specified in claim 20.

To enable the present invention to be more clearly understood, a preferred embodiment thereof will now be described, purely by way of example and without restrictive intent, with reference to the attached figures, of which:

FIG. 3 is an exploded view of the device of FIG. 1, with parts removed for clarity;

FIG. 4 is a perspective view of a detail of the device of FIG. 3;

FIG. 5 is a graph showing characteristics of parts of the device of FIG. 2;

In the example of embodiment described below, the invention is used for monitoring the blood temperature during a dialysis treatment.

Figure 1:
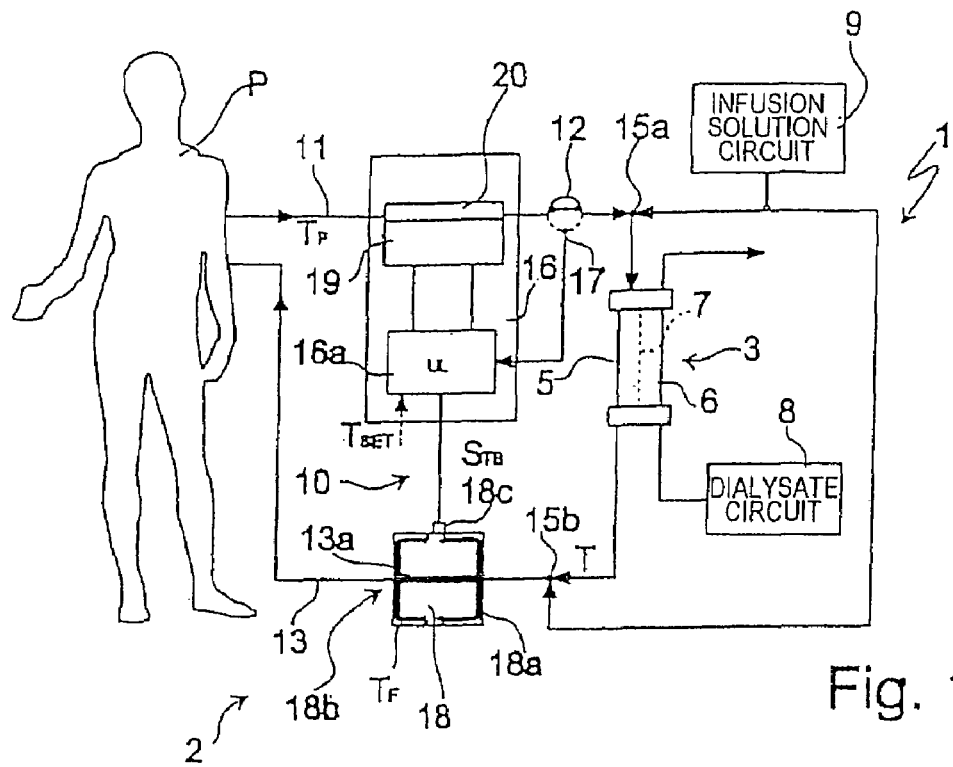
FIG. 1 is a schematic view, with parts removed for clarity, of a dialysis machine equipped with a blood temperature measuring device constructed according to the present invention.

In FIG. 1, the number 1 indicates the whole of a dialysis machine connected to a patient P. The machine 1 comprises an extracorporeal blood circuit 2, a filter 3 including a blood compartment 5 and a dialysate compartment 6 separated by a semi-permeable membrane 7, a dialysate circuit 8 connected to the dialysate compartment 6, an infusion circuit 9 and equipment 10 for regulating the blood temperature.

The extracorporeal blood circuit 2 comprises an arterial branch 11, in which a peristaltic pump 12 is located, and a venous branch 13. The arterial branch 11 has one end connected to the blood compartment 5 and one end connected to a fistula (not illustrated) in the patient P to collect the blood from the cardiovascular system of the patient P, while the venous branch 13 has one end connected to the blood compartment 5 and an opposite end fitted into the aforesaid fistula (not illustrated) to return the treated blood to the cardiovascular system of the patient P. The branches 11 and 13 are tubes made from plastic material, used, respectively, for supplying the blood to be treated to the compartment 5 and for introducing into the cardiovascular system the treated blood leaving the compartment 5.

The infusion circuit 9 is connected to a pre-dilution node 15a, located ill the arterial branch 11, and to a post-dilution node 15b, located in the venous branch 13, and supplies a controlled quantity of an infusion solution to the extracorporeal circuit 2, in a known way. Alternatively, the infusion circuit 9 is connected only to the pre-dilution node 15a or only to the post-dilution node 15b.

The equipment 10 for regulating the blood temperature comprises a non-invasive device 16 for measuring the blood temperature, located in the arterial branch 11 and provided with a control unit 16a, a state sensor 17 for detecting whether the peristaltic pump 12 is in operation, and a temperature regulating device 18, located in a portion 13a of the venous branch 13 of the extracorporeal circuit 2 downstream of the post-dilution node 15b, in such a way that it combines with the portion 113a to form a heat exchanger. The regulating device 18 is also connected to an output of the device 16 supplying a blood temperature signal $S_{TB}$.

The device 18 regulates the blood temperature in the portion 13a without adding mass to the blood flow. In other words, the regulating device 18 acts on a fluid which is separated physically from the blood and whose temperature $T_F$ is monitored by the unit 16a in a range from 20° C. to 43° C. in such a way as to supply heat to, or remove it from, the blood flowing in the venous branch 13 directly before the blood is returned to the patient P.

The regulating device 18 comprises at least one line 18a, which forms a set of windings or a nest of tubes and provides a seat 18b for housing the portion 13a of the venous branch 13, and a heater/cooler 18c connected to the control unit 16a.

During operation, in the course of the dialysis treatment the blood is collected from the patient P and is conveyed along the extracorporeal circuit 2. The non-invasive device 16 measures the temperature $T_P$ and the control unit 16a controls the regulating device 18, on the basis of a predetermined algorithm, as a function of the temperature $T_P$ and a reference temperature $T_{SET}$ which is set by an operator at the control unit 16a.

For example, the control unit 16a compares the temperature $T_P$ with the reference temperature $T_{SET}$, which is generally 37° C., and calculates the temperature difference $\Delta T$ between the temperature $T_P$ and the reference temperature $T_{SET}$. At the start of the dialysis treatment, the regulating device 18 keeps the temperature $T_F$ of the fluid at a value equal to the reference temperature $T_{SET}$, while the temperature $T_D$ of the dialysate is regulated in such a way as to optimize the haemodialysis treatment. During the haemodialysis treatment, the blood temperature T in the extracorporeal circuit 2 varies as a result of the heat exchange with the surrounding environment, with the dialysate, and with the fluid conveyed within the regulating device 18, and as a function of the reaction of the patient P to the materials used in the treatment of the blood.

The temperature $T_P$ is measured by the non-invasive device 16, for example, at relatively short time intervals during the dialysis treatment, and the control unit 16a calculates the temperature difference $\Delta T$ at the same frequency as that of the measurement of the temperature $T_P$. When the temperature difference $\Delta T$ between the temperature $T_P$ and the reference temperature $T_{SET}$ takes a negative value, the fluid temperature $T_F$ is increased in such a way as to supply heat to the blood in the portion 13a, while when the temperature difference $\Delta T$ takes a positive value the fluid temperature $T_F$ is reduced in such a way as to remove heat from the blood in the portion 13a. The repetition of the procedure described above at short time intervals makes it possible to rapidly stabilize the temperature $T_P$, in other words the temperature of the patient P, at a value close to the reference temperature $T_{SET}$, whenever the temperature $T_P$ varies with respect to the reference temperature $T_{SET}$.

The sensor 17 detects the state of operation of the pump 12 and emits a signal to indicate when the pump 12 is operational and when it is stopped. If the signal emitted by the sensor 17 indicates that the pump 12 is in a stopped state, the control unit 16a keeps the value of $T_F$ equal to the reference temperature $T_{SET}$; if, on the other haled, the signal indicates that the pump 12 is in an operational state, the fluid temperature $T_F$ is regulated as a function of the temperature difference $\Delta T$ according to the procedure described above.

In a variant of the operation, the reference temperature. $T_{SET}$ is not fixed, but varies during the dialysis-treatment according to a specified profile.

Figure 2:
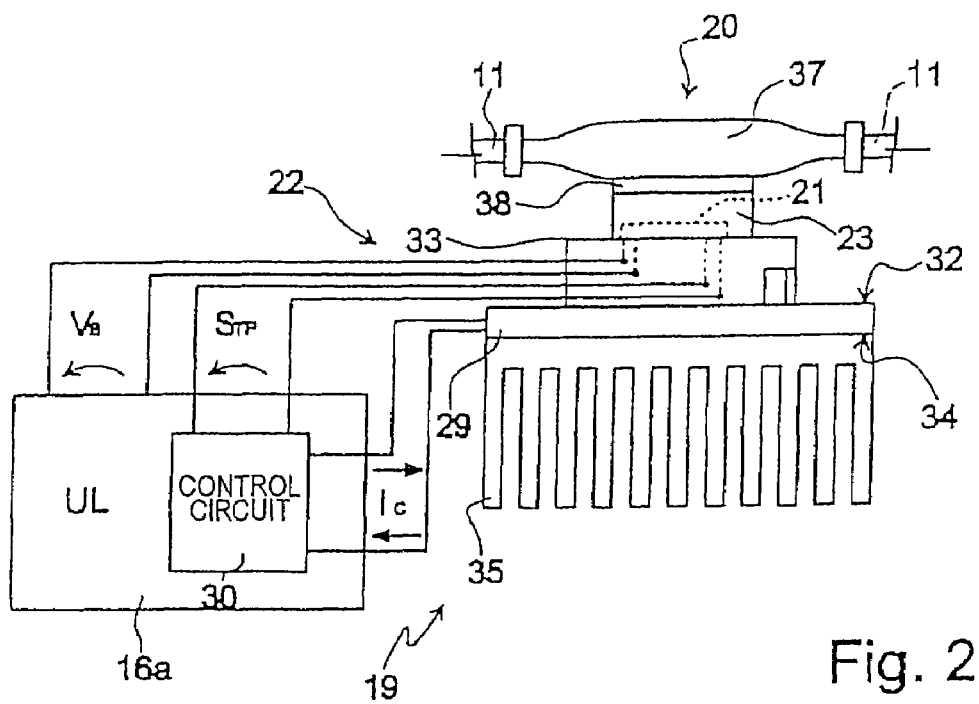
FIG. 2 is a schematic view in side elevation of the measuring device of FIG. 1.

As illustrated in FIGS. 2 and 3, the device 16 comprises a temperature sensor 19, a line 20 fitted in the arterial branch 11 and connected to the sensor 19, and the digital and/or analogue control unit 16a.

Figure 6:
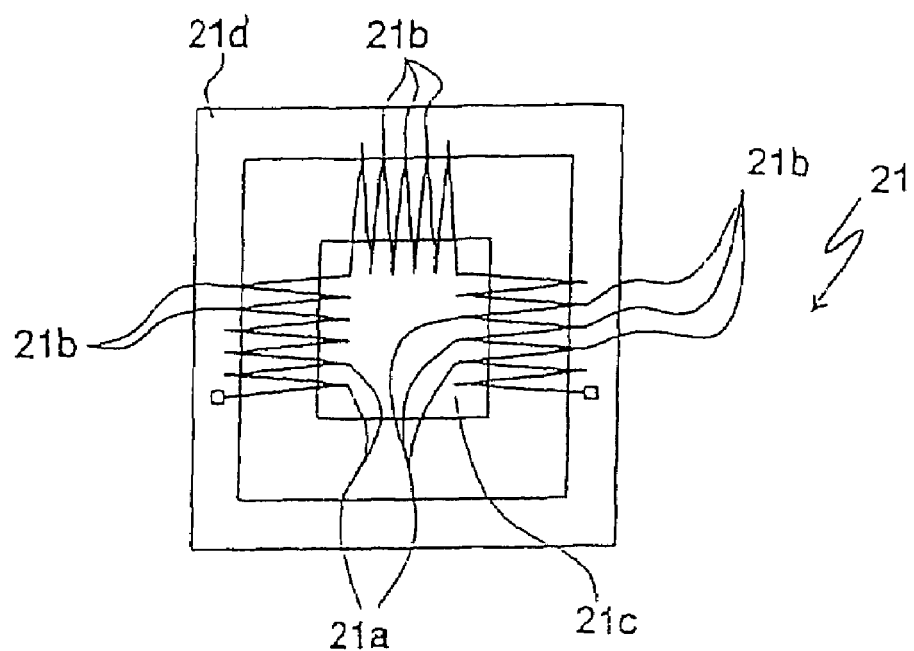
FIG. 6 is a partial schematic view of the detail of FIG. 4.

In greater detail, the sensor 19 comprises a thermopile 21 and a temperature control device 22. The thermopile 21 is housed within a casing 23 (FIG. 4), in a window 24 formed in the said casing 23, and has a pair of measuring terminals 25 connected to the control unit 16a. Between these terminals 25 there is a voltage $V_B$ correlated with the intensity of the electromagnetic radiation striking the thermopile 21 through the window 24 and having a predetermined measurable waveband $B_S$, at least partially included in the infrared band IR (FIG. 5). The operating principle of a thermopile is based on the Seebeck effect. In particular, the thermopile 21 preferably has a plurality of hot junctions 21a and cold junctions 21b connected together in series, as shown in FIG. 6. The hot junctions 21a are located in an area of absorption 21c which absorbs the incident electromagnetic radiation and modifies its own temperature as a result. The cold junctions 21b are supported by a support 21d of semiconductor material placed in contact with the casing 23 (FIG. 4) in which the thermopile 21 is housed. The voltage $V_B$ generated by the thermoelectric effect is a function of the temperature difference between the hot junctions 21a and the cold junctions 21b, in other words between the absorption area 21c and the support 21d. In order to have a voltage $V_B$ which is different from zero and dependent solely on the intensity of the electromagnetic radiation, and in order to have a high signal-to-noise ratio as well, the temperature of the support 21d, on which the cold junctions 21b are located, must be kept at a value sufficiently lower than the operating temperature range within which the thermopile 21 is to be used. For this purpose, use is made of the control device 22 which keeps the casing 23 and consequently the support 21d at a controlled and constant operating temperature, in the range from 5° C. to 15° C. and preferably at 10° C. With reference to FIGS. 2-4, the control device 22 comprises a thermistor 28 (FIG. 4), a solid-state heat pump 29 and a control circuit 30, preferably integrated in the control unit 16a (FIG. 2). The thermistor 28 is located within the casing 23 and is thermally connected to the cold junctions 21b of the thermopile 21 by means of the casing 23 and the support 21d; additionally, the thermistor 28 has a pair of terminals 31 connected to the control circuit 30 and supplying an electrical signal $S_{TP}$, correlated with the operating temperature of thermopile 21. The heat pump 29 is a thermoelectric module, for example a Peltier cell, which causes heat to be transferred between its two opposite surfaces when an electrical current passes through it, and therefore has a cold surface 32 and a hot surface 34 (FIGS. 2 and 3). The cold surface 32 is connected to the casing 23 of the thermopile 21 by means of a heat-conducting support 33 (made from copper, for example), which is pierced so that it can house the thermopile 21. The hot surface 34 is connected to a heat sink 35 to promote the dispersion of the heat extracted by the said heat pump 29. The heat pump 29 also has a pair of terminals 36 connected to the control circuit 30, which, in a known way, supplies a control current $I_C$ correlated with the electrical signal $S_{TP}$.

As shown in FIGS. 2 and 3, the line 20, in which the blood collected from the patient P flows, comprises a connecting portion 37, facing the thermopile 21 and permeable by the electromagnetic radiation in the measurable band $B_S$. In greater detail, the connecting portion 37 is of discoid shape and is completely superimposed on the window 24 of the casing 23 in which the thermopile 21 is housed, in such a way that it completely covers the solid angle of view of the thermopile 21. Additionally, the connecting portion 37 is made from a material having negligible absorbance and high transmittance in the measurable band $B_S$ and in a temperature range from 30° C. to 40° C. Preferably, this material is chosen from high-density polyethylene, low-density polyethylene and poly(4-methyl-1-pentene) (PMP). Thus the fraction of electromagnetic radiation emitted by the blood of the patient P in the temperature range from 30° C. to 40° C. and striking the thermopile is maximized.

A filter 38, comprising a sheet of a material which is essentially opaque to electromagnetic radiation outside a pass band $B_P$ lying within the measurable band $B_S$ (FIG. 5), is interposed between the thermopile 21 and the line 20 (FIGS. 2 and 3). In particular, the filter 38 is supported by the casing 23, and has a first face 39 positioned so that it covers the window 24, and a second face 40, opposite the first face 39 and facing the connecting portion 37 of the line 20. In the embodiment of the invention described herein, the filter 38 is made from suitably treated germanium, and the pass band $B_P$ is in the range from 8 μm to 14 μm (infrared).

During the dialysis treatment, the blood collected from the cardiovascular system of the patient P flows through the line 20 and emits electromagnetic radiation in the measurable band $B_S$. A fraction of the electromagnetic radiation emitted through the filter 38 and the window 24 strikes the thermopile 21, thus contributing to the determination of the value of the voltage $V_B$ between the terminals 25. In greater detail, the variations of the voltage $V_B$ are due exclusively to the variations of intensity of the electromagnetic radiation which is emitted by the blood flowing in the connecting portion 37 and which strikes the thermopile 21. This is because, since the connecting portion 37 is positioned so that it entirely covers the solid angle of view of the thermopile 21 through the window 24, the flow of electromagnetic radiation through the window 24 is essentially due solely to the electromagnetic radiation emitted by the blood flowing in the connecting portion 37; additionally, the casing 23 of the thermopile 21 is kept at a constant known temperature by means of the device 22, and consequently makes a constant contribution to the voltage $V_B$.

The intensity of the radiation is also correlated with the temperature $T_P$ of the body by which it is emitted, in other words the blood of the patient P. More specifically, the total power of the emitted infrared radiation is a function of the temperature of the radiating body, according to the Stefan-Boltzmann law. The intensity of the emitted radiation increases with an increase in the temperature of the radiating body. In the case in question, the filter 38 selects only the electromagnetic radiation lying within the pass band $B_P$, and the voltage $V_B$ generated by the thermopile 21 depends on the energy absorbed in this pass band $B_P$.

The temperature $T_P$ can therefore be determined on the basis of the value of the voltage $V_B$, according to a known relation of the following type:

$$T_P = F(V_B) + T_0 \qquad (1)$$

where $F(V_B)$ is an experimentally determined function and $T_0$ is the operating temperature at which the casing 23, the support 21d and the cold junctions 21b of the thermopile 21 are all maintained.

In ordinary operating conditions, the variations of the temperature $T_P$ are not more than a few degrees Celsius, and therefore the relation (1) can be approximated by the relation:

$$T_P = T_0 + K^* V_B \qquad (2)$$

where K is a known constant, since it is experimentally determined.

Figure 7:
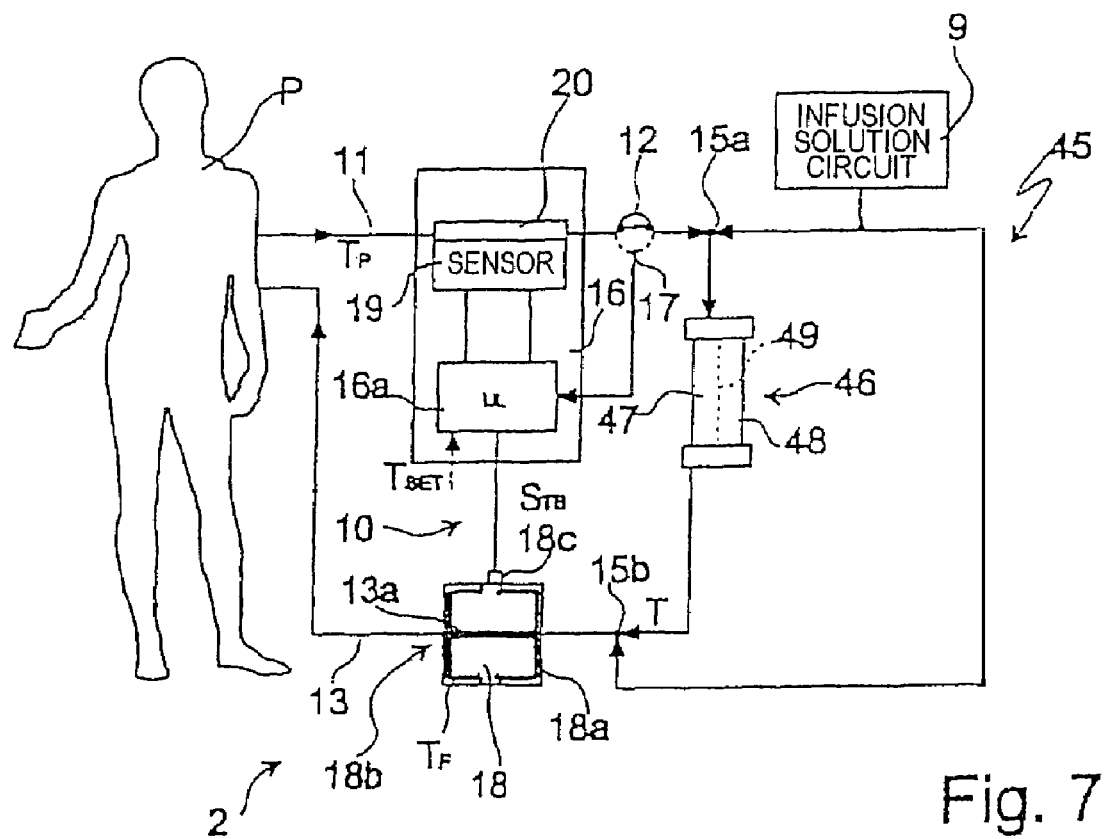
FIG. 7 is a schematic view, with parts removed for clarity, of a dialysis machine equipped with a blood temperature measuring device constructed according to a variant of the present invention.

With reference to FIG. 7, the number 45 indicates a haemofiltration machine comprising the extracorporeal circuit 2 and a haemofiltration filter 46 comprising a blood-compartment 47 and a compartment 48 separated by a semi-permeable membrane 49. The machine 45 is equipped with the blood monitoring equipment 10 and, in particular, is provided with the non-invasive device 16.

The machine 45, can carry out pure haemofiltration treatments and haemofiltration treatments in pre- and/or post-dilution.

The equipment 10 applied to the machine 45 is completely identical to that associated with the machine 1, and its operation is also identical.

The equipment 10 is particularly advantageous in that it can be connected to any type of blood purification machine, and does not require adaptation to the type of purification treatment in use.

Finally, modifications and variations can clearly be applied to the device described without departure from the scope of the present invention. In the first place, the use of the invention is not limited to dialysis machines alone, but can be extended to all cases in which a circuit for extracorporeal blood circulation is used. It is also possible to use infrared radiation measuring devices other than those described, such as devices made from semiconductor material with PN junctions. The non-invasive device could also be provided with a dedicated control unit, separate from that which is used to control the other parts of the equipment for regulating the blood temperature. The heat pump used can also be different from a Peltier cell. As an alternative to the use of a heat pump, it is possible to directly compensate the signal from the thermopile 21 by using the temperature of the casing 23, which can be measured by means of the thermistor 28.

The invention claimed is:

1. A control apparatus for an extracorporeal blood circuit, said extracorporeal blood circuit being connected to a blood purification machine, said extracorporeal blood circuit further comprising an arterial branch connected to at least one blood treatment element and a venous branch connected to at least one blood treatment element, the control apparatus comprising:

a non-invasive device for measuring a blood temperature, said non-invasive measuring device comprising:

a line fitted in the arterial branch upstream of said blood treatment element for receiving blood from a patient, a temperature sensor connected to said line and generating a first signal indicative of a first blood temperature of the blood flowing in said line, said temperature sensor having an electromagnetic radiation intensity measuring device, and said line having a connecting portion of discoid shape facing said electromagnetic radiation intensity measuring device, said connecting portion being permeable to electromagnetic radiation in a first wave band, said first signal corresponding to an intensity of said electromagnetic radiation in said first wave band, a temperature regulating device for regulating the blood temperature in the extracorporeal blood circuit, said device being connected to a portion of the venous branch downstream from said blood treatment element, and a control unit connected to the temperature regulating device and configured to regulate a blood temperature in the extracorporeal blood circuit as a function of the first blood temperature and a reference temperature.

2. An apparatus according to claim 1, wherein said regulating device, is combined with said portion of the venous branch to form a heat exchange.

3. An apparatus according to claim 1, wherein said temperature regulating device comprises a line for conveying a fluid which can be heated to a fluid temperature lying within a specified range, about 37° C.

4. An apparatus according to claim 1, wherein said temperature regulating device has a seat configured to house said portion of the venous branch.

5. An apparatus according to claim 1, wherein said extracorporeal blood circuit is connected to a pump to convey the blood along the extracorporeal blood circuit, the apparatus comprising a sensor for detecting an operating state of the pump; the control unit keeping the fluid temperature substantially equal to said predetermined temperature when the pump is not in operation.

6. An apparatus according to claim 1, wherein said venous branch has a post-dilution node; said portion of the venous branch being located downstream of said post-dilution node.

7. An apparatus according to claim 1, wherein said blood treatment element comprises a hemodialysis filter, said hemodialysis filter comprising a blood compartment and a dialysate compartment within which a dialysate flows.

8. An apparatus according to claim 1, wherein said blood treatment element comprises a hemodialysis filter comprising a blood compartment and a dialysate compartment within which a dialysate flows, and a pre- or post-dilution node for the introduction of a replacement fluid.

9. An apparatus according to claim 1, wherein said blood treatment element comprises a hemofiltration filter.

10. An apparatus according to claim 1, wherein said blood treatment element comprises a hemofiltration filter and a pre- or post-dilution node for the introduction of a replacement fluid.

11. An apparatus according to claim 1, wherein said control unit regulates the blood temperature in the extracorporeal blood circuit as a function of the first blood temperature and the reference temperature at predetermined time intervals.

12. An apparatus according to claim 1, or 11, wherein said control unit regulates the overall temperature as a function of the difference between the first blood temperature and the reference temperature.

13. An apparatus according to claim 1, wherein said measuring device is housed within a casing, the measuring device being configured behind a window formed in said casing; said connecting portion of discoid shape being completely superimposed on said window, to cover a solid angle of view of said measuring device.

14. An apparatus according to claim 1, wherein said measuring device comprises a thermopile having at least one hot junction and at least one cold junction.

15. An apparatus according to claim 14, wherein said temperature sensor comprises a temperature controller, said temperature controller maintaining the at least one cold junction at a controlled temperature.

16. An apparatus according to claim 15, wherein said temperature controller comprises:

a thermistor connected thermally to the cold junction of said measuring device, said thermistor supplying a second signal, said second signal corresponding to said controlled temperature;

a solid state heat pump, having a low temperature surface thermally connected to said measuring device and a high temperature surface; and a control circuit connected to said thermistor, the control circuit configured to receive said second signal, said control circuit also being connected to said heat pump to supply a control signal correlated with said second signal.

17. An apparatus according to claim 16, wherein said heat pump comprises a Peltier cell.

18. An apparatus according to claim 17, comprising a heat sink element placed in contact with said high temperature surface of said heat pump.

19. An apparatus according to claim 18, wherein said controlled temperature is a constant temperature in the range from 5° C. to 15° C.

20. An apparatus according to claim 1, wherein said connecting portion is made from a material which, in said first wave band, has a substantially constant transmittance and an absorbance substantially equal to zero.

21. An apparatus according to claim 1, wherein said connecting portion is made from a material having an essentially constant transmittance in a temperature range from 30° C. to 40° C.

22. An apparatus according to claim 1, wherein said connecting portion is made from a material chosen from a group including high-density polyethylene, low-density polyethylene, and poly(4-methyl-1-pentene).

23. An apparatus according to claim 1, further comprising a filter interposed between said measuring device and said connecting portion of said line.

24. An apparatus according to claim 23, wherein said filter comprises a sheet of material being substantially opaque to electromagnetic radiation outside a second wave band and lying within said first wave band.

25. An apparatus according to claim 24, wherein said second wave band is in a range from 8 μm to 14 μm.

26. An apparatus according to claim 24, wherein said filter includes germanium.

27. An apparatus according to claim 24, wherein said filter has one face facing said connecting portion of said line.

28. An apparatus according to claim 24, wherein an infrared radiation band includes at least a portion of said first wave band.

* * * * *

UNITED STATES PATENT AND TRADEMARK OFFICE
CERTIFICATE OF CORRECTION

PATENT NO. : 7,648,475 B2  Page 1 of 1
APPLICATION NO. : 10/500336
DATED : January 19, 2010
INVENTOR(S) : De Cicco et al.

It is certified that error appears in the above-identified patent and that said Letters Patent is hereby corrected as shown below:

Column 7, line 64, "claim 1, or 11," should read --claim 1 or 11,--.

Signed and Sealed this

Twentieth Day of April, 2010

David J. Kappos
*Director of the United States Patent and Trademark Office*